(12) United States Patent
Mason et al.

(10) Patent No.: US 10,008,091 B2
(45) Date of Patent: Jun. 26, 2018

(54) PROCESSING AN ALERT SIGNAL OF A MEDICAL DEVICE

(71) Applicant: KONINKLIJKE PHILIPS N.V., Eindhoven (NL)

(72) Inventors: Jonathan David Mason, Eindhoven (NL); Dzmitry Viktorovich Aliakseyeu, Eindhoven (NL); Peter Bingley, Eindhoven (NL); Angelique Carin Johanna Maria Brosens-Kessels, Eindhoven (NL); Paul Augustinus Peter Kaufholz, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 14/891,379

(22) PCT Filed: May 26, 2014

(86) PCT No.: PCT/EP2014/060830
§ 371 (c)(1),
(2) Date: Nov. 16, 2015

(87) PCT Pub. No.: WO2014/195171
PCT Pub. Date: Dec. 11, 2014

(65) Prior Publication Data
US 2016/0086476 A1    Mar. 24, 2016

(30) Foreign Application Priority Data
Jun. 3, 2013   (EP) ..................... 13170265

(51) Int. Cl.
*G08B 21/18*   (2006.01)

(52) U.S. Cl.
CPC ............. *G08B 21/18* (2013.01); *G16H 10/60* (2018.01); *G16H 15/00* (2018.01)

(58) Field of Classification Search
CPC .... G06F 19/322; G06F 19/3487; G08B 21/18
See application file for complete search history.

(56) References Cited

U.S. PATENT DOCUMENTS

| 6,092,102 A | 7/2000 | Wagner |
| 7,649,454 B2 * | 1/2010 | Singh ..................... G08B 21/24 340/539.11 |

(Continued)

FOREIGN PATENT DOCUMENTS

| JP | 2010220759 | 10/2010 |
| RU | 82416 | 4/2009 |
| WO | 2012/131546 | 10/2012 |

OTHER PUBLICATIONS

"mVisum Alert Alarm Management System", http://www.mvisum.com/mvisumalert.php.

(Continued)

*Primary Examiner* — Quan-Zhen Wang
*Assistant Examiner* — Rajsheed Black-Childress

(57) ABSTRACT

A system (100) is provided for processing an alert signal of a medical device associated with a patient. The alert signal comprises medical information (122) representing an alert generated by the medical device to alert a healthcare professional to a state of the patient and/or the medical device. The system obtains the alert signal (024) of the medical device (020). The system comprises an interpretation subsystem (140) which accesses an interpretation database (040). Using the interpretation database (040), the interpretation subsystem (140) generates an interpreted version (142) of the alert by using the interpretation data (044) to interpret the medical information. This interpreted version of the alert provides an explanation of the alert in a manner (Continued)

suitable for a non-professional caretaker of the patient. The system then generates an output signal (162) comprising said interpreted version for a mobile device to enable communicating the interpreted version of the medical information to the non-professional caretaker via the mobile device (060). As such, the non-professional caretaker is provided with information he/she can understand.

18 Claims, 2 Drawing Sheets

(56) References Cited

U.S. PATENT DOCUMENTS

| | | | |
|---|---|---|---|
| 8,306,830 B1* | 11/2012 | Renuart | G06Q 50/22 |
| | | | 705/2 |
| 8,447,626 B2 | 5/2013 | Sun | |
| 8,700,431 B2 | 4/2014 | Ryan | |
| 9,050,031 B2 | 6/2015 | Collins et al. | |
| 9,223,299 B2* | 12/2015 | Jenkins | G05B 9/02 |
| 2005/0144042 A1 | 6/2005 | Joffe et al. | |
| 2006/0058612 A1 | 3/2006 | Ashok et al. | |
| 2006/0135907 A1* | 6/2006 | Remde | A61M 5/142 |
| | | | 604/67 |
| 2006/0214786 A1* | 9/2006 | Bixler | G06Q 50/22 |
| | | | 340/539.12 |
| 2007/0282629 A1* | 12/2007 | Plambeck | G06F 17/30864 |
| | | | 705/2 |
| 2008/0154513 A1 | 6/2008 | Kovatchev et al. | |
| 2009/0089100 A1 | 4/2009 | Nenov et al. | |
| 2009/0171225 A1 | 7/2009 | Gadodia et al. | |
| 2010/0223070 A1* | 9/2010 | Kelly | G06F 19/322 |
| | | | 705/3 |
| 2011/0156886 A1 | 6/2011 | Clinkscales et al. | |
| 2011/0172550 A1 | 7/2011 | Martin | |
| 2012/0078654 A1* | 3/2012 | DeGruttola | G06F 19/327 |
| | | | 705/2 |
| 2013/0162426 A1* | 6/2013 | Wiesner | A61B 5/746 |
| | | | 340/539.1 |
| 2015/0222756 A1* | 8/2015 | Tsaliah | H04W 4/02 |
| | | | 455/404.2 |

OTHER PUBLICATIONS

Kaczmarek, M. et al. "The Use of Mobile Devices in the Care and Home Monitoring of the Elderly and the Sick", Information Technologies in Biomedicine, Lecture Notes in Computer Science vol. 7339, 2012, pp. 525-536.

* cited by examiner

PROCESSING AN ALERT SIGNAL OF A MEDICAL DEVICE

CROSS-REFERENCE TO PRIOR APPLICATIONS

This application is the U.S. National Phase application under 35 U.S.C. § 371 of International Application No. PCT/EP2014/060830, filed on May 26, 2014, which claims the benefit of European Patent Application No. 13170265.6, filed on Jun. 3, 2013. These applications are hereby incorporated by reference herein.

FIELD OF THE INVENTION

The invention relates to a system and a method for processing an alert signal of a medical device. The invention further relates to a computer program product comprising instructions for causing a processor system to perform said method.

BACKGROUND OF THE INVENTION

Medical devices such as patient monitors typically make available medically relevant information to healthcare professionals. Such information may be about a state of the patient, a state of the medical device, etc. The information may serve to alert the user to said state, and may take various forms. For example, if a patient monitor determines the state of a patient is deteriorating, e.g., by a heart rate of the patient being irregular, the patient monitor may generate an alert by displaying a warning, sounding an alarm, etc. The healthcare professional is thus informed to attend the patient, check on the patient monitor, etc.

Various systems are known for providing such medical information to a mobile device of a healthcare professional to ensure communication of the information to the healthcare professional. For example, a product titled mVisum Alert Management System is said to have the following functionality, according to a webpage consulted on Apr. 2, 2013 at the web-address http://www.mvisum.com/mvisumalert.php. An alarm is generated by a patient monitor or telemetry device and sent to the mVisum Server which then push delivers it to the mobile device. mVisum Alert application on the mobile device receives the alarm data and sounds a unique audible ringtone that corresponds to the criticality of the alarm. The alarm details, color coded by alarm severity, are displayed on the handheld device. Additional data displayed include a scrollable waveform showing the alarm event.

US 2008/0154513 A1 describes an enhancement of existing home blood glucose (BG) monitoring devices by introducing an intelligent data interpretation component capable of predicting and alerting the user to periods of increased risk for hyperglycemia, hypoglycemia, increased glucose variability, and ineffective testing. For that purpose, self-monitored (SM) BG measurements are evaluated and warnings for the next time period are issued. Such warnings may take the form of messages such as "Your blood sugar is typically low before lunch". US 2008/0154513 A1 is thus from the field of home monitoring devices.

Disadvantageously, the abovementioned mVisum system does not address the following situation. When a patient is admitted to hospital and family, friends or other non-professional caretakers are staying with the patient, such as in the case when parents are staying with their baby in a neonatal ward, the number of medical devices which monitor and provide care services for the patient can often be overwhelming for such non-professional caretakers. This situation is exacerbated when these medical devices begin to generate alerts, e.g., by sounding audible alarms or displaying various information onscreen. Non-professional caretakers are often unaware of what is happening and do not know what to do, thereby giving rise to anxiety and/or stress. Further exacerbating the situation is the fact that healthcare professionals such as nurses and doctors may rush over to attend to the patient for one type of alarm but not for another type of alarm. Yet another cause of anxiety and/or stress may be that, in some hospitals, the name of the patient may be suddenly displayed on a hospital screen without the non-professional caretaker knowing why.

SUMMARY OF THE INVENTION

It would be advantageous to obtain a system or method which is able to reduce or entirely avoid anxiety and/or stress rising in the non-professional caretaker in the abovementioned situations.

To better address this concern, a first aspect of the invention provides a system for processing an alert signal of a medical device, the medical device being associated with a patient, the medical device generating an alert for alerting a healthcare professional to a state of the patient and/or the medical device, comprising:
  an input interface for obtaining the alert signal of the medical device, the signal comprising medical information for communication to a healthcare professional, the medical information representing the alert;
  an interpretation subsystem for:
i) accessing an interpretation database, the interpretation database comprising interpretation data being indicative of interpreted versions of different types of medical information representing different types of alerts, each interpreted version providing an explanation of a respective type of alert in a manner suitable for a non-professional caretaker of the patient; and
ii) generating an interpreted version of the alert from the signal by using the interpretation data to interpret the medical information; and
  an output interface for communicating the interpreted version of the alert to the non-professional caretaker via a mobile device by generating an output signal comprising said interpreted version for the mobile device.

In a further aspect of the invention, a mobile device and a medical device are provided, each comprising the system set forth.

In a further aspect of the invention, a method is provided for processing an alert signal of a medical device, the medical device being associated with a patient, the medical device generating an alert for alerting a healthcare professional to a state of the patient and/or the medical device, comprising:
  obtaining the alert signal of the medical device, the alert signal comprising medical information for communication to a healthcare professional, the medical information representing the alert;
  accessing an interpretation database, the interpretation database comprising interpretation data being indicative of interpreted versions of different types of medical information representing different types of alerts, each interpreted version providing an explanation of a respective type of alert in a manner suitable for a non-professional caretaker of the patient;

generating an interpreted version of the alert from the signal by using the interpretation data to interpret the medical information; and communicating the interpreted version of the alert to the non-professional caretaker via a mobile device by generating an output signal comprising said interpreted version for the mobile device.

In a further aspect of the invention, a computer program product is provided comprising instructions for causing a processor system to perform the method set forth.

The above measures provide an input interface for obtaining a signal which is generated by a medical device. The medical device is involved in the monitoring or treatment of a patient or performs any another medical task related to the patient. The signal comprises medically relevant information which is intended for being communicated to and interpreted by a healthcare professional. As such, the information may require a medical background for interpretation, or in general, be difficult to interpret for a non-professional caretaker.

Moreover, an interpretation subsystem is provided which obtains the medical information of the signal from the input interface. The interpretation subsystem is arranged for accessing an interpretation database, e.g., on an internal or external storage device. The interpretation database comprises interpretation data which is indicative of interpreted versions of different types of medical information, and in particular, of the type that is normally communicated to a healthcare professional. A non-limiting example of the interpretation data is a look-up table which allows obtaining an interpreted version of a particular type of medical information by looking up said type of medical information.

Each interpreted version presents the respective type of medical information such that it is suitable for communication to the non-professional caretaker, i.e., it is a suitable interpretation. As such, the interpreted version of said medical information may not require a medical background for interpretation, or in general, be easy to interpret by the non-professional caretaker. The interpretation subsystem is arranged for using the interpretation data to interpret the medical information which is obtained from the signal. As a result, the interpretation subsystem obtains an interpreted version of the medical information.

An output interface is provided for communicating the interpreted version of the medical information to the non-professional caretaker. For that purpose, the output interface generates an output signal which comprises the interpreted version of the medical information. The output signal is generated for communication to a mobile device of the non-professional caretaker. As such, the non-professional caretaker can be informed of the interpreted version of the medical information via the mobile device.

The above measures have the following effect. By obtaining the signal of the medical device, the system receives medical information which is intended for communication to the healthcare professional and which, when received by the healthcare professional, may trigger activity relating to the patient which in turn may give rise to anxiety and/or stress in the non-professional caretaker. By being provided with interpretation data, the system is enabled to generate an interpreted version of the medical information which presents the medical information in a manner suitable for the non-professional caretaker. By generating an output signal comprising said interpreted version for a mobile device of the non-professional caretaker, the medical information can be provided to the non-professional caretaker at his/her current location, e.g., in the hospital. Effectively, the system functions as a translator by translating medical information which intended for interpretation by the healthcare professional to information which is suitable for interpretation by the non-professional caretaker. By being provided with the interpreted version of the medical information, the non-professional caretaker is provided with information he/she can understand. Advantageously, if the medical information triggers activity relating to the patient, the non-professional caretaker is informed about said activity, thereby reducing and possibly preventing anxiety and/or stress. Advantageously, the healthcare professional is less distracted by having to update the non-professional caretaker on the current situation.

The signal constitutes an alert for alerting the healthcare professional to a state of the patient and/or the medical device. The inventors have recognized that alerts such as patient alerts or device alerts trigger various types of activity relating to the patient and/or the medical device that may give rise to anxiety and/or stress in the non-professional caretaker. Here, the term patient alert refers to an alert for alerting the healthcare professional to a state of the patient, and the term device alert refers to an alert for alerting the healthcare professional to a state of the medical device itself. An example of the former is an apnea warning, whereas an example of the latter is a malfunction warning. The system thus interprets the medical information contained in or constituted by the alert and provides the non-professional caretaker with an interpreted version of said information.

The interpretation subsystem is arranged for generating the interpreted version of the medical information to provide an explanation of the alert to the non-professional caretaker. By explaining the patient alert or the device alert to the non-professional caretaker, additional contextual information is given of the alert which may further help preventing anxiety and/or stress in the non-professional caretaker.

Optionally, the medical device generates the alert in the form of an auditory or visual alarm, the input interface is arranged for receiving sensor data of the auditory or visual alarm, and the system is arranged for using a video or audio analysis technique to identify the alert signal in the sensor data and the medical information from the alert signal.

Optionally, the input interface receives the alert signal from the medical device in the form of a network message.

Optionally, the interpretation subsystem is arranged for limiting a frequency of the providing of the explanation for a particular type of alert by providing the explanation a limited number of times. The non-professional caretaker is thus only provided a limited number of times with the explanation of a particular type of alert, for example only once. It is thereby prevented that the non-professional caretaker is repeatedly provided with said explanations even though he/she has already been made aware of the context, consequences, etc, of the particular type of alert.

Optionally, the interpretation subsystem is arranged for generating the interpreted version of the alert to comprise instructions for the non-professional caretaker to take an action with respect to the patient and/or the medical device. The system thus provides instructions to non-professional caretaker in response to the medical information. This aspect of the invention is based on the insight that the non-professional caretaker is frequently nearby the patient, e.g., sitting besides the patient's bed. As such, the non-professional caretaker may be able to take action with respect to the patient and/or the medical device earlier than the healthcare professional. By providing instructions to the non-professional caretaker to take such actions, the actions may be carried out earlier. Advantageously, after having been carried out by the non-professional caretaker, it is not needed for the healthcare professional to carry out such actions themselves anymore.

Optionally, the interpretation subsystem is arranged for i) estimating a location of the mobile device, and ii) generating the interpreted version of the alert in dependence on said location. By estimating the location of the mobile device, e.g., in a manner known per se from the field of mobile location estimation, an estimate of the location of the non-professional caretaker is obtained since typically a mobile device is nearby its user. Having obtained said estimate of the location, the system is enabled to generate the interpreted version of the medical information in a location-aware manner. For example, the system may determine whether or not to provide an interpreted version of the medical information depending on the estimate of the location of the mobile device.

Optionally, the interpretation subsystem is arranged for adjusting a detail and/or type of the interpreted version of the alert based on the location. Advantageously, the system is enabled to increase the detail of the interpretation when the non-professional caretaker is nearby the patient and reduce the detail when the non-professional caretaker is far away. Similarly, the system is enabled to only provide interpretations which instruct the non-professional caretaker to take action with respect to the patient and/or medical device when the non-professional caretaker is nearby the patient.

Optionally, the interpretation subsystem is arranged for estimating the location to establish if the non-professional caretaker is located in one of the group of: a room of the patient, a hospital of the patient and outside of said hospital. It has been found to be of particular relevance to distinguish between said locations when generating the interpreted version of the medical information based on the location of the non-professional caretaker.

Optionally, the system further comprises a patient schedule interface for accessing a patient schedule of the patient, and the interpretation subsystem is further arranged for generating pre-alert information based on the patient schedule for informing the non-professional caretaker about a scheduled event associated with the patient. By having access to the patient schedule, the system is enabled to determine activities related to the patient which may give rise to anxiety and/or stress in the non-professional caretaker. For example, if healthcare professionals are scheduled to visit the patient whilst the non-professional caretaker is unaware of this fact, their sudden appearance may give rise to anxiety and/or stress. By accessing the patient schedule of the patient, the system is provided with information about such scheduled events. Accordingly, the system is enabled to inform the non-professional caretaker of the scheduled event ahead of time.

Optionally, the scheduled event is one of the group of: a patient visit to the patient, a medical examination of the patient, a medical treatment of the patient and a medical diagnosis of the patient.

Optionally, the output interface is constituted by a mobile device interface arranged for communicating with the mobile device using a short-range communication technique. The output interface can thus directly communicate with the mobile device via the short-range communication technique. Short-range communication techniques, such as Near Field Communication (NFC) and Bluetooth, are well suited for communication with the mobile device since their limited range ensures that the interpretation by the system automatically ceases when the mobile device leaves the range of the short-range communication technique. Advantageously, the interpretation automatically ceases when it is likely to be less relevant to the non-professional caretaker, e.g., after leaving the hospital. Advantageously, the communication with the mobile device is inherently relatively secure in that parties outside of said range cannot eavesdrop on the communication.

Optionally, the mobile device interface is arranged for enabling the non-healthcare professional to pair the mobile device with the system using the short-range communication technique. By pairing the mobile device with the system, the system is enabled to determine to which mobile device the output signal is to be provided. Advantageously, the communication with the mobile device is inherently relatively secure in that parties outside of said range cannot pair their mobile devices with the system.

Moreover, a system may be provided for processing a signal of a medical device, the system comprising:
  an input interface for obtaining the signal of the medical device, the medical device being associated with a patient, the signal comprising medical information for communication to a healthcare professional;
  an interpretation subsystem for:
i) accessing an interpretation database, the interpretation database comprising interpretation data being indicative of interpreted versions of different types of medical information, each interpreted version presenting a respective type of medical information in a manner suitable for a non-professional caretaker of the patient; and
ii) generating an interpreted version of the medical information from the signal by using the interpretation data to interpret the medical information; and
  an output interface for communicating the interpreted version of the medical information to the non-professional caretaker via a mobile device by generating an output signal comprising said interpreted version for the mobile device.

In a further aspect of the invention, a mobile device and a medical device are provided, each comprising the system set forth.

Moreover, a method may be provided for processing a signal of a medical device, the method comprising:
  obtaining the signal of the medical device, the medical device being associated with a patient, the signal comprising medical information for communication to a healthcare professional;
  accessing an interpretation database, the interpretation database comprising interpretation data being indicative of interpreted versions of different types of medical information, each interpreted version presenting a respective type of medical information in a manner suitable for a non-professional caretaker of the patient;
  generating an interpreted version of the medical information from the signal by using the interpretation data to interpret the medical information; and
  communicating the interpreted version of the medical information to the non-professional caretaker via a mobile device by generating an output signal comprising said interpreted version for the mobile device.

It will be appreciated by those skilled in the art that two or more of the above-mentioned embodiments, implementations, and/or aspects of the invention may be combined in any way deemed useful.

Modifications and variations of the method and/or the computer program product, which correspond to the described modifications and variations of the system, can be carried out by a person skilled in the art on the basis of the present description.

The invention is defined in the independent claims. Advantageous yet optional embodiments are defined in the dependent claims.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Figure 1:
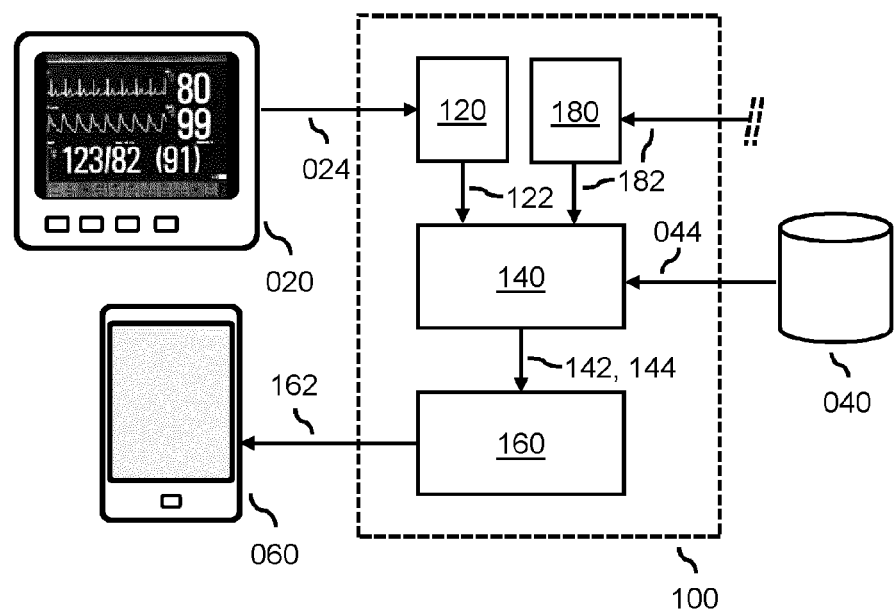
FIG. 1 shows a system for processing a signal of a medical device and for providing a result of said processing in the form of an output signal to a mobile device.

FIG. 1 shows a system 100 for processing a signal of a medical device. The system 100 comprises an input interface 120 for obtaining a signal 024 of the medical device 020. The medical device 020 is associated with a patient. As shown by way of example in FIG. 1, the medical device 020 may be a patient monitor which measures, e.g., the heart rate and blood pressure of the patient. Alternatively, the medical device 020 may be any other medical device 020 which performs a medical task with respect the patient. The input interface 120 is shown to directly receive the signal 024 from the medical device 020. Alternatively, the input interface 120 may receive the signal 024 via one or more intermediary devices, e.g., one or more elements of a hospital network.

The signal 024 comprises medical information for communication to a healthcare professional. The signal 024 may comprise said medical information in various forms. For example, the signal 024 may comprise data such as descriptive text, an alert code, etc. It is noted that the medical device 020 may be a known medical device 020 providing a known signal 024. For example, the medical device 020 may sound an auditory alarm in case of a medical emergency. At the same time, the medical device 020 may signal the medical emergency to other systems or devices by sending a network message. For example, if the medical device 020 determines that respiration has stopped for longer than a preset apnea time, the medical device 020 may send a network message comprising the text "***APNEA mm:ss sec", with "mm:ss" denoting the Apnea duration in minutes and seconds. Instead of an alert, the signal 024 may also provide a warning or other medical information which in itself does not constitute a medical emergency. Also, the signal 024 may relate to the medical device 020 itself rather than to the patient. For example, the medical device 020 may send a network message comprising the text "BATT MALFUNCT" after determining that its battery is malfunctioning. It is noted that such information is considered medical information since it is medically relevant, i.e., it concerns information that is likely to affect the patient.

The system 100 further comprises an interpretation subsystem 140. The interpretation subsystem 140 is arranged for accessing interpretation data 044 on an interpretation database 040. In the example of FIG. 1, the interpretation database 040 is shown to be located outside of the system 100, e.g., on an external storage device. Alternatively, the interpretation database 040 may be located inside of the system 100, e.g., on an internal storage device. The interpretation data 044 is indicative of interpreted versions of different types of medical information for communication to the healthcare professional. In particular, the interpretation data 044 is indicative of interpreted versions which each present a respective type of medical information in a manner suitable for a non-professional caretaker of the patient. The interpretation subsystem 140 is arranged for generating an interpreted version 142 of the medical information from the signal 024 by using the interpretation data 044 to interpret the medical information. For that purpose, the interpretation subsystem 140 is shown to obtain the medical information 122 from the signal from the input interface 120.

The system 100 further comprises an output interface 160 for communicating the interpreted version 142 of the medical information to the non-professional caretaker. For that purpose, the output interface 160 generates an output signal 162 comprising said interpreted version 142 of the medical information. FIG. 1 further shows the output interface 160 providing the output signal 162 to a mobile device 060 of the caretaker. The output signal 162 may be provided wirelessly to the mobile device 060, e.g., using a mobile communication technique. For that purpose, the output interface 160 may comprise a mobile transmitter or may be arranged for providing the output signal 162 to a mobile transmitter. In this respect, it is noted that the system 100 may not have to determine which mobile device 060 is associated with the caretaker of the patient, but may rather comprise an address, e.g., a mobile phone number, IP address, etc, to which the output signal 162 is to be provided.

An operation of the system 100 may be briefly explained as follows. The input interface 120 obtains the signal 024 of the medical device 020. For example, the medical device 020 may send the signal 024 to the input interface 120. The interpretation subsystem 140 accesses the interpretation data 044. The interpretation subsystem 140 then uses the interpretation data to interpret the medical information from the signal, thereby generating an interpreted version 142 of the medical information. Subsequently, the output interface 160 generates an output signal 162 comprising the interpreted version 142 of the medical information for a mobile device 060 to enable communicating the interpreted version 142 of the medical information to the non-professional caretaker via the mobile device 060. The output interface 160 may then provide the output signal to the mobile device 060.

Figure 2:
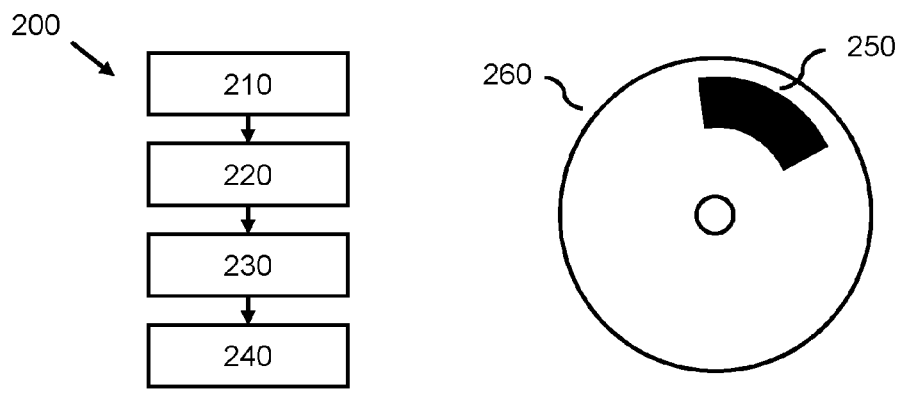
FIG. 2 shows a method for processing the signal of the medical device.

FIG. 2 shows a method 200 for processing a signal of a medical device. The method 200 may correspond to an operation of the system 100. However, the method 200 may also be performed in separation of the system 100, e.g., using a different system.

The method 200 comprises, in a step titled "OBTAINING SIGNAL OF MEDICAL DEVICE", obtaining 210 the signal of the medical device, the medical device being associated with a patient, the signal comprising medical information for communication to a healthcare professional. The method 200 further comprises, in a step titled "ACCESS- ING INTERPRETATION DATA", accessing 220 an interpretation database, the interpretation database comprising interpretation data being indicative of interpreted versions of different types of medical information, each interpreted version presenting a respective type of medical information in a manner suitable for a non-professional caretaker of the patient. The method 200 further comprises, in a step titled "INTERPRETING INFORMATION", generating 230 an interpreted version of the medical information by using the interpretation data to interpret the medical information from the signal. The method 200 further comprises, in a step titled "GENERATING OUTPUT SIGNAL FOR MOBILE DEVICE", generating 240 an output signal comprising said interpreted version for a mobile device of the non-professional caretaker for communicating the interpreted version of the medical information to the non-professional caretaker via the mobile device.

Although not shown in FIG. 2, the method 200 may further comprise a step titled "COMMUNICATING OUTPUT SIGNAL TO MOBILE DEVICE", the step comprising communicating the output signal to the mobile device of the non-professional caretaker. Moreover, it will be appreciated that the steps of the method 200 may be performed in any suitable order. In particular, the step of accessing 220 the interpretation data may be performed before or during the step of obtaining 210 the signal of the medical device.

Figure 3:
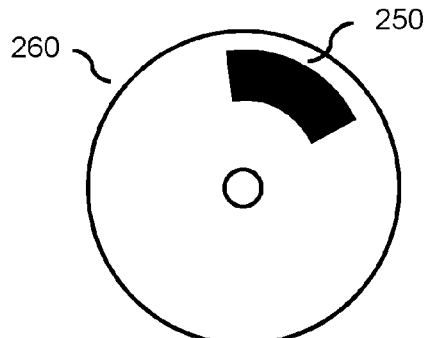
FIG. 3 shows a computer program product comprising instructions for causing a processor system to perform the aforementioned method.

FIG. 3 shows a computer program product 250 comprising instructions for causing a processor system to perform the aforementioned method 200. The computer program product 250 may be comprised on a computer readable medium 260, for example in the form of as a series of machine readable physical marks and/or as a series of elements having different electrical, e.g., magnetic, or optical properties or values.

Referring further to FIG. 1, the system 100 may access and use various types of interpretation data 044 in the interpreting of the medical information 122 from the signal 024. For example, the interpretation data 044 may be constituted by a look-up table which enables the interpretation subsystem 140 to look up the medical information 122. As corresponding entry, the look-up table may then comprise the interpreted version 142 of the medical information. Accordingly, the interpretation subsystem 140 may generate the interpreted version of the medical information by simply reading out said entry of the look-up table. The interpretation data 044 may also be constituted by a set of pre-defined rules which enable the interpretation subsystem 142 to generate the interpreted version 142 of the medical information by applying the rules to the medical information. Yet another example of the interpretation data 044 is medical data as provided by medical textbooks, guidelines, protocols, etc. The interpretation subsystem 140 may be arranged for using reasoning techniques to derive the interpreted version 142 of the medical information from the medical information 122 using the medical data as knowledge base. It is noted that such reasoning techniques are known per se from the field of reasoning engines.

The signal 024 may constitute an alert 024 for alerting the healthcare professional to a state of the patient and/or the medical device 020. Moreover, the interpretation subsystem 140 may be arranged for generating the interpreted version 142 of the medical information to provide an explanation of the alert 024 to the non-professional caretaker. The interpretation subsystem 140 may obtain the explanation directly from the interpretation data 044, e.g., by looking up the medical information 122 from the signal 024. Alternatively, the interpretation subsystem 140 may itself generate the explanation, e.g., using the aforementioned reasoning techniques and medical data as knowledge base. An example of the medical information 122 obtained from the medical device 020 and its interpreted version provided by the interpretation subsystem 140 is the following:

| Medical information | Interpreted version |
| --- | --- |
| AFIB DETECTED | The patient monitor has detected atrial fibrillation which means that an irregular heart beat has been detected. As a standard procedure, a nurse has been alerted to check on the patient. |

The interpretation subsystem 140 may be arranged for limiting a frequency of how often the explanation is provided for a particular type of alert 024. For example, the interpretation subsystem 140 may provide the explanation when a particular type of alert is received and subsequently interpreted by the system 100 for a first time. For all subsequent alerts of the same type, the subsystem 140 may not provide the explanation. Rather, the interpretation subsystem 140 may provide a brief interpretation or no interpretation at all. For example, in the earlier example of the detected atrial fibrillation, the alert of "AFIB DETECTED" may be interpreted the second and following times as "The patient monitor has detected atrial fibrillation", without providing the abovementioned explanation.

The interpretation subsystem 140 may be arranged for generating the interpreted version 142 of the medical information to instruct the non-professional caretaker to take an action with respect to the patient and/or the medical device 020. An example of the medical information 122 obtained from the medical device 020 and such interpreted version of the medical information provided by the interpretation subsystem 140 are the following:

| Medical information | Interpreted version |
| --- | --- |
| CO2 NO TUBING | The patient monitor has detected that the sample tubing is disconnected. Please inspect the sample tubing to make sure that the sample tubing is not kinked or twisted. |
| BAG NEAR EMPTY | The infusion pump has detected that its bag is nearly empty. In approximately 10 minutes time, the infusion pump will sound an auditory alarm. You do not need to act as a nurse will be alerted by the auditory alarm to replace the bag. |

The interpretation subsystem 140 may be arranged for including additional information in the interpreted version 142 of the medical information, such as, e.g., a name of the healthcare professional. For example, the interpreted version 142 of the medical information may be "Nurse Smith will attend the patient shortly".

A further example of the interpreted version 142 of the medical information itself may be a traffic light interpretation which indicates by means of a green color or similar visual metaphor that everything is in order, i.e., "OK" with the patient, and by means of a red color or similar visual metaphor that a medical emergency is taking place.

Referring further to FIG. 1, the system 100 may comprise a patient schedule interface 180 for accessing a patient schedule 182 of the patient. In the example of FIG. 1, the patient schedule 182 is shown to be accessed from outside of the system 100, e.g., on an external storage device. For example, the patient schedule interface 180 may access the patient schedule 182 on a database of a Hospital Information System (HIS). Alternatively, the patient schedule 182 may be accessed inside of the system 100, e.g., on an internal storage device. The patient schedule 182 is indicative of one or more scheduled events associated with the patient. For example, the patient schedule 182 may be indicative whether, and if so, when a patient visit to the patient is scheduled. Additionally or alternatively, the patient schedule 182 may be indicative whether, and if so, when a medical examination, a medical treatment and/or a medical diagnosis of the patient is scheduled.

The interpretation subsystem 140 may be arranged for generating pre-alert information 144 based on the patient schedule for informing the non-professional caretaker about a scheduled event associated with the patient. For that purpose, the interpretation subsystem 140 is shown to access the patient schedule 182 via the patient schedule interface 180. Accordingly, the interpretation subsystem 140 may identify a scheduled event of the patient and generate pre-alert information 144 to inform the non-professional caretaker about said scheduled event. For that purpose, the output interface may communicate the pre-alert information to the non-professional caretaker by generating a further output signal comprising the pre-alert information 144 for the mobile device 060. The interpretation subsystem 140 may automatically identify upcoming scheduled events. Accordingly, the non-professional caretaker may be automatically informed about upcoming scheduled events.

An example of a scheduled event identified from the patient schedule and the pre-alert information generated by the interpretation subsystem 140 is the following:

| Scheduled event | Pre-alert information |
|---|---|
| 14:30-15:30 Ward Round | A ward round is scheduled today at 14:30. This is a weekly scheduled event in which Dr. Johnson will provide an update on the recent history, clinical examination and review of patient. |

Figure 4A:
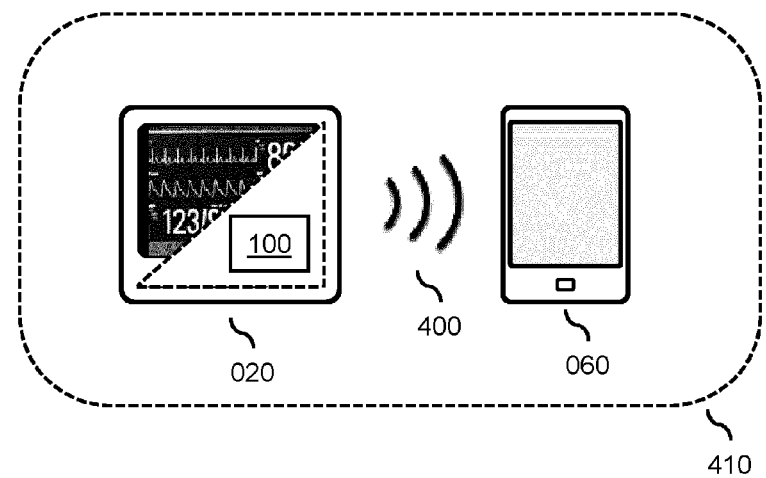
FIG. 4a shows the system being comprised in the medical device and communicating with the mobile device using a short-range communication technique.
Figure 4B:
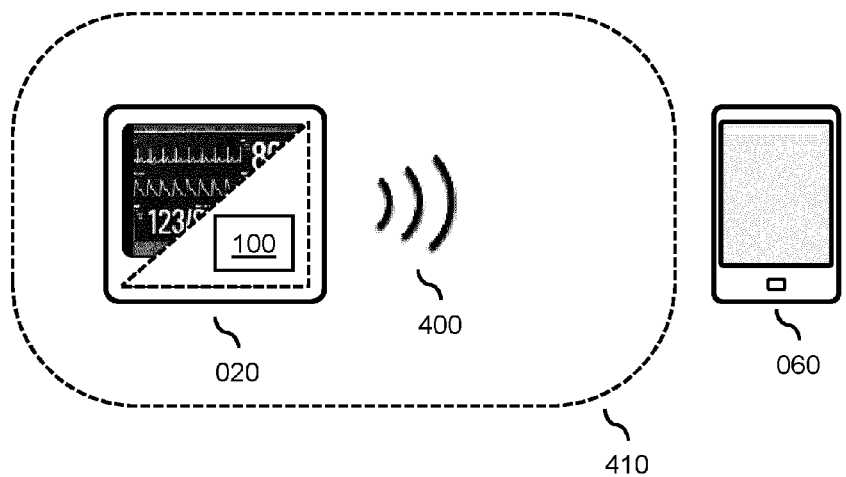
FIG. 4b shows the mobile device being outside of communication range of the short-range communication technique.

The system 100 may be a stand-alone system which may be arranged for receiving and interpreting the signals from existing medical devices in a clinical environment. The system 100 may also be included in the mobile device 060 of the non-professional caretaker. The system 100 may also be included in the medical device 020. An example of the latter is shown in FIGS. 4a and 4b. Here, the medical device 020 comprises the system 100, as shown by way a cut-away depiction of a part of the medical device 020. Thus, the medical device 020 comprises the input interface 120, the interpretation subsystem 140 and the output interface 160. The input interface 120 may be an internal interface, i.e., for communicating internally within the medical device 020.

FIG. 4a further shows the system 100 of the medical device 020 communicating with the mobile device 060 using a short-range communication technique. For that purpose, the output interface 160 may be constituted by a mobile device interface. Non-limiting examples of suitable short-range communication techniques include NFC, Bluetooth and ZigBee. The communication using the short-range communication technique is schematically indicated in FIG. 4a by means of radio waves 400. Accordingly, the system 100 may provide the output signal 162 to the mobile device 060 via the short-range communication technique. The communication may be subject to the mobile device 060 having been paired with the system 100. Here, the term paired refers to the establishing of a relationship between the system 100 and the mobile device 060. For that purpose, the mobile device interface may be arranged for enabling the non-healthcare professional to pair the mobile device 060 with the system using the short-range communication technique. The paring may be subject to, or involve, the mobile device 060 authenticating itself or the non-professional caretaker authenticating him/herself using the mobile device 060.

Further shown in FIG. 4a is a range 410 of the short-range communication technique with respect to the system 100 of the medical device 020. The mobile device 060 is shown to be located within the range 410 of the system 100. Accordingly, communication between the system 100 and the mobile device 060 is possible, i.e., it is possible for the mobile device interface of the system 100 to communicate the interpreted version 142 of the medical information to the non-professional caretaker by providing the output signal 162 comprising said interpreted version to the mobile device 060 of said caretaker.

FIG. 4b shows a same situation as shown in FIG. 4a, except that the mobile device 060 is now located outside the range 410 of the system 100. This may be due to, e.g., the non-professional caretaker leaving the ward, leaving the hospital, etc. Accordingly, communication between the system 100 and the mobile device 060 is not possible using the short-range communication technique. This situation may be a desired situation in that the interpretation of the medical information 122 from the signal 024 may be inherently location-aware: it automatically cease when the non-professional caretaker and thus the mobile device 060 carried by the caretaker leaves the vicinity of the patient and thus of the medical device.

Although not shown in FIG. 4a or 4b, the system 100 may also use a long-range communication technique such as a cellular communication technique to communicate with the mobile device 060. The system 100 may use the long-range communication technique in addition to the aforementioned short-range communication technique, e.g., when the mobile device 060 is outside of the range 410 of the short-range communication technique. The interpretation subsystem 140 may be arranged for adjusting a detail and/or type of the interpreted version 142 of the medical information based on whether the long-range or the short-range communication technique is used. For example, the interpretation subsystem 140 may omit providing the interpreted version of non-urgent medical information when the non-professional caretaker is outside of the range 410 of the short-range communication technique. Another example is that the interpretation subsystem 410 may omit instructing the non-professional caretaker to take an action with respect to the patient and/or the medical device 020 when the non-professional caretaker is outside of said range.

The interpretation subsystem 140 may also be arranged for estimating a location of the mobile device 060, and generating the interpreted version 142 of the medical information in dependence on said location. The interpretation subsystem 140 may estimate the location of the mobile device 060 manner known per se from the field of mobile location estimation. For example, the mobile device 060 may use Global Positioning System (GPS) or Wi-Fi-based location techniques to obtain its own location and may provide the location to the interpretation subsystem 140. Another example is that the mobile device 060 may make use of Wi-Fi access points within a hospital, and the interpretation subsystem 140 may estimate the location of the mobile device 060 by determining to which access point the mobile device 060 is connected. Having estimated the location of the mobile device 060, the interpretation subsystem 140 may adjust a detail and/or type of the interpreted version 142 of the medical information based on the location. For example, the interpretation subsystem may distinguish between whether the mobile device 060 and thus the non-professional caretaker are estimated to be in a room of the patient, in the hospital or outside of the hospital. The system 100 may also estimate or otherwise obtain location information on the healthcare professional. Accordingly, the interpretation subsystem 140 may adjust the detail and/or type of the interpreted version 142 of the medical information based on whether the healthcare professional and the non-professional caretaker are co-located, e.g., in the room of the patient. For example, the interpretation subsystem 140 may only instruct the non-professional caretaker to take an action with respect to the patient and/or the medical device 020 if the healthcare professional is not in the room of the patient, e.g., in another ward.

It is further noted that, instead of directly receiving the signal 024 from the medical device 020, e.g., via a network message, the input interface 120 may alternatively or additionally obtain sensor data from a sensor such as a video camera and/or a microphone. Such sensors may be directed at the medical device 020 to sense signals generated by the medical device 020 such as auditory or visual alarms. For example, the input interface 120 may receive video data from a video camera of a closed-circuit television (CCTV) system within the hospital. The signal 024 may be comprised in such sensor data in visual or auditory form, for example, in the form of as pixel data showing a display output of the medical device 020. The system 100 may be arranged for using a video or audio analysis technique to identify the signal 024 in the sensor data and subsequently the medical information 122 from the signal 024. Such techniques are known per se from the technical fields of image analysis, video analysis and audio analysis. For example, the system may use an image analysis technique to optically recognize characters of a visual warning on a display of the medical device 020, the visual warning constituting the signal 024 from the medical device 020 and the characters constituting the medical information of the visual warning.

It is noted that, in general, the output interface 160 may be arranged for communicating the interpreted version of the medical information on request of the non-professional caretaker. In particular, the output interface 160 may be arranged for, on request, communicating the interpreted version of recent status information concerning the patient which has been recently obtained by the system 100, i.e., from a recently received signal 024. Accordingly, the non-professional caretaker may "ask" the system 100 on the status of the patient. The system 100 may communicate the status in various ways, i.e., using various interpretations, such as color codes, simple text or other abstract information.

Moreover, in general, the signal 024, the medical information 122 and/or the interpreted version 142 of the medical information may be logged by the system, e.g., to enable healthcare professionals to see who has been visiting or attending the patient.

It will be appreciated that the present invention may be advantageously used to provide a meaningful link between a patient monitor of a patient and a mobile device of a non-professional caretaker of the patient. The patient monitor may send information to the mobile device which is interpreted to convey information from the patient monitor in a clear and meaningful manner to the non-professional caretaker. The present invention may be used to provide reassurance and updates to the non-professional caretaker, thereby putting his/her mind to rest; it may even help the non-professional caretaker to feel a part of the treatment.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware.

The mere fact that certain measures are recited in mutually different dependent claims does not indicate that a combination of these measures cannot be used to advantage.

The invention claimed is:

1. A system for processing an alert signal of a medical device, the medical device being associated with a patient, the medical device generating an alert for alerting a healthcare professional to a state of the patient and/or the medical device, comprising:
   an input interface that receives the alert signal of the medical device, the alert signal accompanying an alert in the form of an auditory or visual alarm generated by the medical device and comprising medical information that is to be sent to a healthcare professional, the medical information representing the alert;
   an interpretation database comprising a non-transitory computer-readable medium storing interpretation data for generating interpreted versions of medical information representing alerts generated by the medical device wherein the interpreted versions comprise explanations of alerts generated by the medical device in a manner suitable for a non-professional caretaker of the patient;
   an interpretation subsystem comprising a processor and a non-transitory computer-readable medium storing instructions that, when executed by the processor, causes the processor to:
      estimate a location of a mobile device using one or more of a location provided by the mobile device, WiFi based locating, and attempting communication with the mobile device via a short range communication technique;
      access the interpretation database and receive therefrom interpretation data corresponding to the alert; and
      generate an interpreted version of the alert by using the received interpretation data to interpret the medical information representing the alert, wherein the interpreted version of the alert is different from the medical information that is to be sent to the healthcare professional and provides an explanation of the alert in a manner suitable for a non-professional caretaker of the patient; and
   an output interface that communicates the interpreted version of the alert to the non-professional caretaker via the mobile device if the estimated location of the mobile device is within a range of the medical device.

2. The system of claim 1, wherein the input interface is arranged for receiving sensor data of the auditory or visual alarm, and wherein the system is arranged for using a video or audio analysis technique to identify the alert signal in the sensor data and the medical information from the alert signal.

3. The system of claim 1, wherein the input interface receives the alert signal from the medical device in the form of a network message.

4. The system of claim 1, wherein the interpretation subsystem is arranged for limiting a frequency of the providing of the explanation for a particular type of alert by providing the explanation a limited number of times.

5. The system of claim 1, wherein the interpretation subsystem adjusts a detail and/or type of the interpreted version of the alert based on the estimated location of the mobile device.

6. The system of claim 1, wherein the interpretation subsystem estimates the location to establish if the non-professional caretaker is located in one of the group of: a room of the patient, a hospital of the patient, and outside of the hospital.

7. The system of claim 1, further comprising a patient schedule interface that accesses a patient schedule of the patient, and wherein the interpretation subsystem further generates pre-alert information based on the patient schedule for informing the non-professional caretaker about a scheduled event associated with the patient.

8. The system of claim 7, wherein the scheduled event is one of the group of: a patient visit to the patient, a medical examination of the patient, a medical treatment of the patient, and a medical diagnosis of the patient.

9. The system of claim 1, wherein:
   the output interface comprises a mobile device interface that communicates with the mobile device using a short-range communication technique, and
   the interpretation subsystem estimates the location of the mobile device by attempting communication with the mobile device via the short-range communication technique, and
   the output interface communicates the interpreted version of the alert to the non-professional caretaker via the mobile device if the mobile device is within range of the short-range communication technique.

10. The system of claim 9, wherein the mobile device interface enables the non-healthcare professional to pair the mobile device with the system using the short-range communication technique.

11. A non-transitory computer-readable medium that comprises a program that, when executed by a processing system, causes the processing system to:
   obtain an alert signal from a medical device, the alert signal accompanying an alert in the form of an auditory or visual alarm generated by the medical device and comprising medical information that is to be communicated to a healthcare professional, the medical information representing the alert;
   access an interpretation database comprising a non-transitory computer-readable medium storing interpretation data for generating interpreted versions of medical information representing alerts generated by the medical device wherein the interpreted versions comprise explanations of alerts generated by the medical device in a manner suitable for a non-professional caretaker of the patient,
   receiving therefrom from the interpretation database an interpreted version of the alert, wherein the interpreted version of the alert is different from the medical information that is to be sent to the healthcare professional and provides an explanation of the alert in a manner suitable for a non-professional caretaker of the patient;
   estimate a location of a mobile device, and
   communicate the interpreted version of the alert to the non-professional caretaker via the mobile device conditional upon the location of the mobile device being within a range of the medical device.

12. The medium of claim 11, wherein the processing system obtains the alert signal from the medical device via a network interface.

13. The medium of claim 11, wherein, in the event of obtaining repetitive alert signals, the program causes the processing system to cease communication of the interpreted version of the alert after a given number of communications.

14. The medium of claim 11, wherein the program further causes the processing system to access a patient schedule of the patient, and to communicate pre-alert information based on the patient schedule to inform the non-professional caretaker about a scheduled event associated with the patient.

15. The medium of claim 11, wherein the program causes the processing system to:
   estimate the location of the mobile device by attempting communication with the mobile device via a short-range communication technique, and
   communicate with the mobile device using the short-range communication technique conditional upon the mobile device being within range of the short-range communication technique.

16. A system for processing an alert signal of a medical device, the medical device being associated with a patient, the medical device generating an alert for alerting a healthcare professional to a state of the patient and/or the medical device, comprising:
   an input interface that receives the alert signal of the medical device, the alert signal accompanying an alert in the form of an auditory or visual alarm generated by the medical device and comprising medical information that is to be sent to a healthcare professional, the medical information representing the alert;
   an interpretation database comprising a non-transitory computer-readable medium storing interpretation data for generating interpreted versions of medical information representing alerts generated by the medical device wherein the interpreted versions comprise explanations of alerts generated by the medical device in a manner suitable for a non-professional caretaker of the patient;
   an interpretation subsystem comprising a processor and a non-transitory computer-readable medium storing instructions that, when executed by the processor, causes the processor to:
      access the interpretation database and receive therefrom interpretation data corresponding to the alert; and
      generate an interpreted version of the alert by using the received interpretation data to interpret the medical information representing the alert, wherein the interpreted version of the alert is different from the medical information that is to be sent to the healthcare professional and provides an explanation of the alert in a manner suitable for a non-professional caretaker of the patient; and
   a short-range communication interface that communicates the interpreted version of the alert to the mobile device if the mobile device is within range of the short-range communication interface.

17. The system of claim 16 wherein the short-range communication interface pairs with the mobile device whereby the short-range communication interface communicates with the paired mobile device.

18. The system of claim 16 wherein the short-range communication interface operates using one of Near Field Communication (NFC), Bluetooth, and ZigBee.

* * * * *